(12) United States Patent
Bäther et al.

(10) Patent No.: US 11,585,783 B2
(45) Date of Patent: Feb. 21, 2023

(54) GAS SENSOR AND GAS-MEASURING DEVICE FOR DETECTING VOLATILE ORGANIC COMPOUNDS

(71) Applicant: Dräger Safety AG & Co. KGaA, Lübeck (DE)

(72) Inventors: Wolfgang Bäther, Lübeck (DE); Stefan Lehmann, Uetersen (DE)

(73) Assignee: Dräger Safety AG & Co. KGaA

( * ) Notice: Subject to any disclaimer, the term of this patent is extended or adjusted under 35 U.S.C. 154(b) by 188 days.

(21) Appl. No.: 17/171,506

(22) Filed: Feb. 9, 2021

(65) Prior Publication Data

US 2021/0164934 A1    Jun. 3, 2021

Related U.S. Application Data

(63) Continuation of application No. 15/523,032, filed as application No. PCT/EP2015/002211 on Nov. 4, 2015, now Pat. No. 10,942,145.

(30) Foreign Application Priority Data

Nov. 7, 2014   (DE) .................. 10 2014 016 394.6

(51) Int. Cl.
 *G01N 27/414*   (2006.01)
 *G01N 33/00*    (2006.01)

(52) U.S. Cl.
 CPC ..... *G01N 27/4141* (2013.01); *G01N 33/0047* (2013.01)

(58) Field of Classification Search
 None
 See application file for complete search history.

(56) References Cited

U.S. PATENT DOCUMENTS 8,668,871 B2   3/2014   Matsumoto et al.

OTHER PUBLICATIONS

German Patent and Trademark Office, German Examination Report for Application No. 102014016394.6, dated Mar. 14, 2022.

*Primary Examiner* — Xiaoyun R Xu
(74) *Attorney, Agent, or Firm* — Design IP

(57) ABSTRACT

A gas sensor 10 has a measuring channel 11 with a gas inlet 12 and with a gas outlet 13, at least one receptor layer 20, a reference electrode 30 and a voltage-controlled analysis unit 50. The reference electrode 30 is capacitively coupled with the receptor layer 20. The reference electrode 30 is connected to the analysis unit 50 in an electrically conductive manner. The receptor layer 20 is formed in measuring channel 11. The measuring channel 11 forms a dielectric layer between the receptor layer 20 and the reference electrode 30. The receptor layer 20 has a support 21 and an analyte-binding layer 22. The present invention provides for the analyte-binding layer 22 to be a self-assembling monolayer (SAM).

11 Claims, 6 Drawing Sheets

FIG. 3a
FIG. 3b
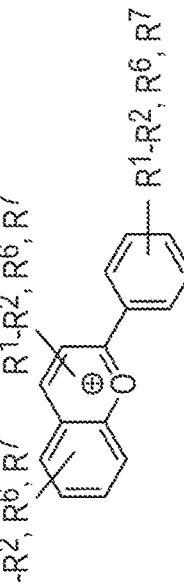
FIG. 3c
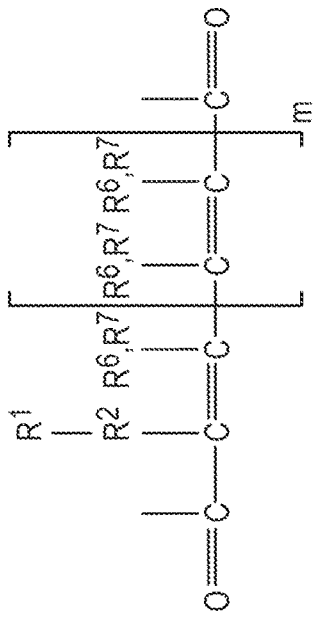
FIG. 3d
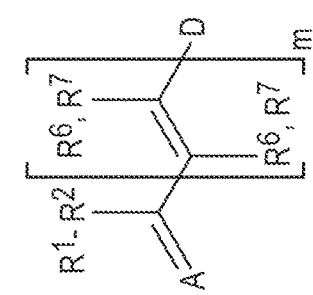
FIG. 3e
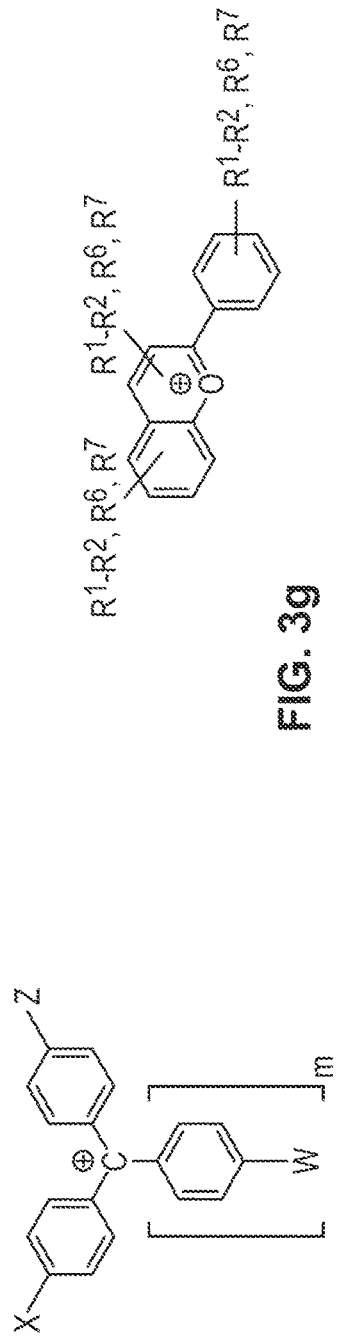
FIG. 3f
FIG. 3g

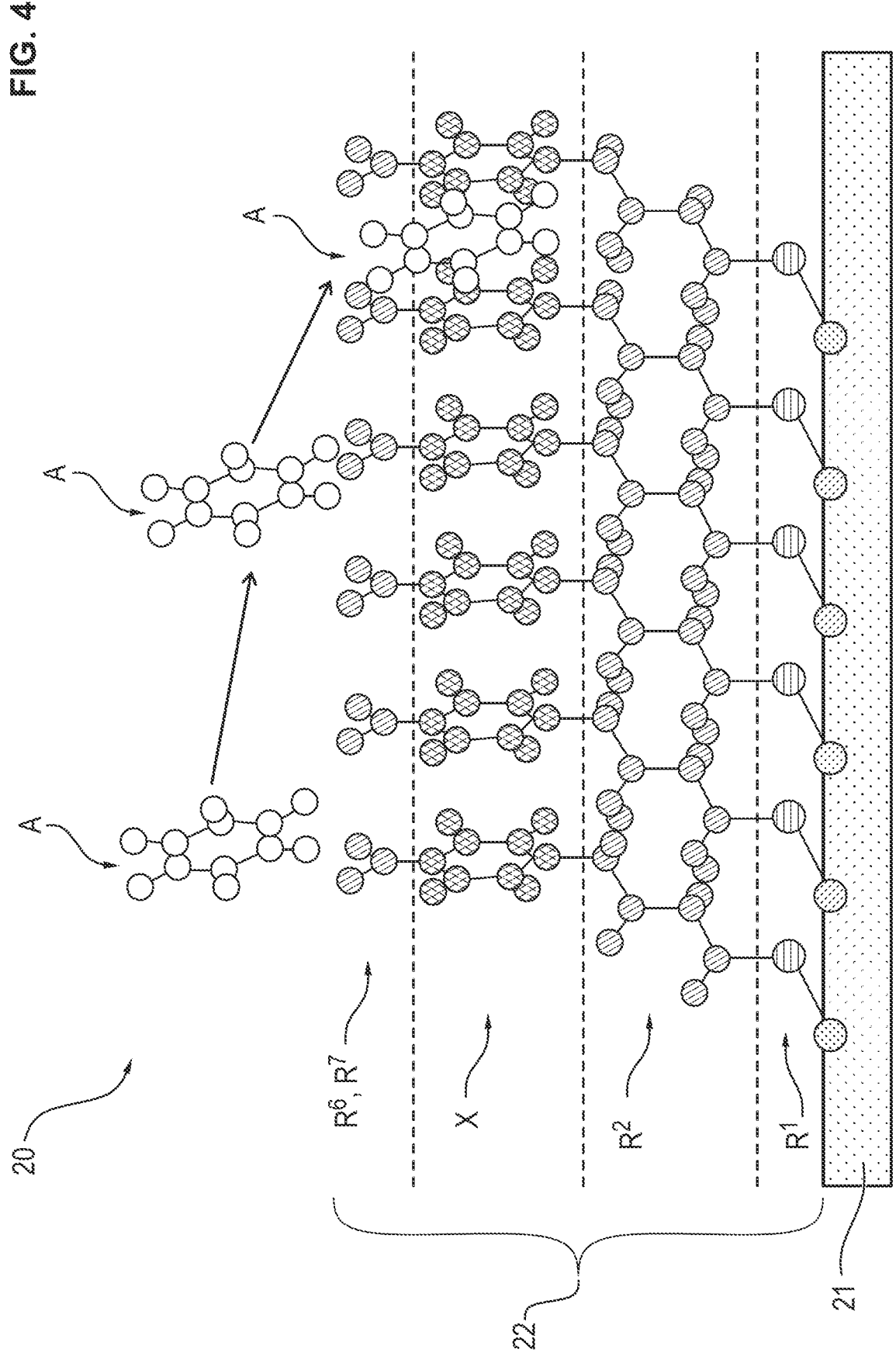

GAS SENSOR AND GAS-MEASURING DEVICE FOR DETECTING VOLATILE ORGANIC COMPOUNDS

CROSS REFERENCE TO RELATED APPLICATIONS

This application is a continuation of U.S. patent application Ser. No. 15/523,032, which is a United States National Phase Application of International Application PCT/EP2015/002211, filed Nov. 4, 2015, and claims the benefit of priority under 35 U.S.C. § 119 of German Application 10 2014 016 394.6, filed Nov. 7, 2014, the entire contents of which are incorporated herein by reference.

FIELD OF THE INVENTION

The present invention pertains to a gas sensor, to a gas-measuring device and to the use of a gas sensor according to the present invention for detecting volatile organic compounds.

BACKGROUND OF THE INVENTION

Gas sensors that are suitable for detecting chemical compounds comprise, in principle, a combination of receptor and transducer. The receptor—e.g., a receptor electrode—can typically interact with the analyte molecules to be detected at the molecular level. A physicochemical property of the receptor, for example, the work function of the receptor surface, changes in the process. The transducer can detect this change and transform it into a—for example, electrical—signal. The electrical signal can then, in turn, be used to trigger an alarm or the like.

For example, semiconductor-based gas sensors are known in this connection, which comprise a field-effect transistor (FET) and a capacitor coupled with the FET (Capacitively Controlled Field Effect Transistor (CCFET)). The capacitor is configured as an air capacitor. One of the two capacitor areas acts as a receptor, the surface of the capacitor area (receptor surface) being able to interact with the analyte molecules to be detected. The measured gas to be tested flows through the capacitor between the capacitor areas and forms the dielectric. If an interaction occurs between the receptor surface and analyte molecules, which are present in the gas being measured, the capacitance of the capacitor changes. This change in capacitance can be transformed into an electrical signal by means of the FET.

U.S. Pat. No. 4,411,741 A provides in this connection a gas sensor, in which a receptor electrode is arranged opposite the gate electrode of an FET and is separated from the gate electrode by an air gap. The gate electrode of the FET and the receptor electrode form the capacitor areas here.

DE 43 33 875 A1 also provides for a semiconductor gas sensor with an FET. However, the analyzing FET or the air gap, in which the layer is arranged, and the air gap, in which the gas-sensitive layer is formed, i.e., the capacitor, are nevertheless electrically coupled with one another. The FET has a gate electrode, which is connected to a sensor electrode in a conductive manner. A gas-sensitive layer is arranged opposite the sensor electrode. The gas-sensitive layer is spaced from the sensor electrode by an air gap and is coupled to the sensor electrode capacitively via the air gap.

EP 2 006 668 A1 likewise provides for such a sensor. The gas-sensitive layer is covered by an additional protective layer here. This additional protective layer is adheringly connected to the gas-sensitive layer, but is permeable to the target gas. This is likewise used to modify strongly nonlinear changes in the measured signal, which changes may occur in certain combinations of gas-sensitive layer and analyte despite a more or less linear change in the target gas concentration, such that the change in the measured signal more or less corresponds to the change in the target gas concentration.

Typical materials of which the receptor layer of such prior-art gas sensors may consist are metals, semiconductors, semiconductor compounds or metal compounds, e.g., platinum, palladium, titanium nitride, copper phthalocyanine, barium titanate, tin dioxide, silver oxide, cobalt oxide, chromium-titanium oxide, gold, potassium iodide or also germanium. The particular material used determines what analytes can be detected. For example, hydrogen can be detected by means of platinum or palladium, while $NO_2$ and other inorganic gases can be detected, among others, with receptor layers consisting of cobalt oxide, tin oxide or copper phthalocyanine. The detection of so-called volatile organic compounds is often problematic, especially if they have a generally relatively inert behavior, e.g., benzene. One reason for this is the fact that the interaction that such organic compounds show with the materials used as the receptor layer often does not take place at all or does so only weakly. Optical sensors are therefore frequently used as an alternative for detecting such compounds. However, these may be highly sensitive to shocks and other mechanical effects. In addition, they often are relatively large.

SUMMARY OF THE INVENTION

Based on this, an object of the present invention is, among other things, to overcome these and other drawbacks of the state of the art and to provide an improved gas sensor. For example, a gas sensor shall be provided that can be suitable for use in a PAM. It is desirable in this connection that volatile organic compounds, especially benzene, be able to be detected with certainty and reliably by means of such a sensor.

In a gas sensor in which the gas sensor has a measuring channel with a gas inlet and with a gas outlet, at least one receptor layer, a reference electrode and an analysis unit, wherein the reference electrode is capacitively coupled with the receptor layer, wherein the reference electrode is connected to the analysis unit in an electrically conductive manner, wherein the receptor layer is formed in the measuring channel, wherein the measuring channel forms a dielectric layer between the receptor layer and the reference electrode, and wherein the receptor layer has a support and an analyte-binding layer, provisions are made according to the present invention for the analyte-binding layer to be a self-assembling monolayer, which consists of molecules according to the general formula $$R^1\text{—}R^2\text{—}X,$$

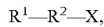

in which $R^1$ is a coupling group, selected from the group containing sulfide, disulfide, sulfinyl, sulfino, sulfo, carbonothiol, thiosulfate, thiocyanate, isothiocyanate, preferably sulfide or thiosulfate, and wherein the molecules of the self-assembling monolayer are coupled each to the support via $R^1$;

wherein the support is a layer consisting of metal, wherein the metal is selected from the group containing gold, platinum, palladium, silver and copper;

wherein $R^2$ is a spacer, selected from the group containing alkane, alkene, alkyne, heteroalkane, heteroalkene, heteroalkyne, substituted alkanes, substituted alkenes, substituted alkynes, substituted heteroalkanes, substituted heteroalkenes, substituted heteroalkynes, ethers, amines; and wherein X is an organic or organometallic group, which can interact with analyte molecules, especially an organic or organometallic group with at least one delocalized π system.

In other words, the analyte-binding layer may be a self-assembling monolayer, which consists of molecules according to the general formula

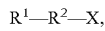

wherein $R^1$ is a coupling group, selected from the group containing sulfide, disulfide, sulfinyl, sulfino, sulfo, carbonothiol, thiosulfate, thiocyanate, isothiocyanate, preferably sulfide or thiosulphate, and wherein the molecules of the self-assembling monolayer are coupled each via an $R^1$ to the support; wherein support is a layer consisting of metal, wherein the metal is selected from the group comprising gold, platinum, palladium, silver and copper; wherein $R^2$ is a spacer, selected from the group containing alkane, alkene, alkyne, heteroalkane, heteroalkene, heteroalkyne, substituted alkanes, substituted alkenes, substituted alkynes, substituted heteroalkanes, substituted heteroalkenes, substituted heteroalkynes, ethers, amines; and wherein X is an organic or organometallic group with at least one delocalized πn system.

The analyte-binding layer may also be a self-assembling monolayer, which consists of molecules according to the general formula

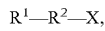

wherein $R^1$ is a coupling group, selected from the group containing sulfide or thiosulfate, and wherein the molecules of the self-assembling monolayer are coupled with the support each via $R^1$; wherein the support is a layer consisting of metal, wherein the metal is selected from the group containing (comprising any of) gold, platinum, palladium, silver and copper; wherein $R^2$ is a spacer, selected from the group containing (comprising any of) alkane, alkene, alkyne, heteroalkane, heteroalkene, heteroalkyne, substituted alkanes, substituted alkenes, substituted alkynes, substituted heteroalkanes, substituted heteroalkenes, substituted heteroalkynes, ethers, amines; and wherein X is an organic or organometallic group with at least one delocalized π system.

A gas to be tested (gas to be measured) can therefore flow into the measuring channel through the gas inlet in all cases and flow out of the measuring channel through the gas outlet. Therefore, the gas to be measured flows through the measuring channel as a flow of gas to be measured. The present invention covers both a gas sensor, through which a flow of gas to be measured is flowing, and a gas sensor without a flow of gas to be measured. The latter may happen, for example, when the gas inlet and/or the gas outlet are closed before mounting the gas sensor, e.g., for transportation purposes or the like. The measuring channel has in any case an inner wall, which defines the interior of the measuring channel. According to the present invention, the receptor layer is part of this inner wall. The receptor layer is thus part of the measuring channel. The gas to be measured, which flows through the measuring channel, flows along the receptor layer. The receptor layer forms a surface, which can interact with an analyte to be detected. The analyte is typically contained in the gas to be measured, which flows as a flow of gas to be measured through the measuring channel. The reference electrode may also be part of the inner wall. The flow of gas to be measured or the measured gas can therefore flow through the measuring channel between the receptor layer and the reference electrode.

The receptor layer is a surface area of a capacitor in this connection. The capacitor is preferably formed by the receptor layer, the reference electrode and the flow of gas to be measured, which acts as a dielectric and by the volume of the measuring channel between the receptor layer and the reference electrode, which volume acts as a dielectric. The reference electrode is thus coupled capacitively with the receptor layer. For example, the receptor layer and the reference electrode may be formed on mutually opposite sides of the measuring channel, preferably on opposite sides of the inner side of the measuring channel. The gas to be measured, i.e., the gas to be tested, flows through the measuring channel, so that the flow of gas to be measured flows through between the receptor layer and the reference electrode. The measuring channel therefore forms a volume between the two surfaces of the capacitor, which volume can act as a dielectric both when gas being measured flows through the measuring channel and when the measuring channel is empty, i.e., in the rather unlikely case in which, e.g., a vacuum is present in the measuring channel. The measuring channel thus acts as a dielectric between the capacitor areas, i.e., the measuring channel forms a dielectric layer. It is favorable in this connection if the measuring channel can be heated. In addition, it is advantageous if the measuring channel is pressure-proof.

The measuring channel may be defined by a cover and an insulation layer. Such a cover and such an insulation layer define at least one part of the volume of the measuring channel. The receptor layer may be formed on the cover. The reference electrode may be embedded in the insulator layer. The analysis unit may likewise be embedded in the insulation layer.

The analysis unit is either current-controlled or voltage-controlled, but it is preferably voltage-controlled. A voltage-controlled analysis unit may be in this connection, for example, a transistor or also another voltage-controlled electronic component, e.g., a voltage-controlled oscillator or the like. It is essential in this connection that the voltage-controlled analysis unit can detect and process changes in the capacitance of the capacitor without the flow of a current being necessary. If an interaction occurs between an analyte and the receptor layer, the work function (i.e., the energy that must be expended to detach an electron from a corresponding material layer) will change on the receptor layer and there will consequently be a change in the capacitance of the capacitor. The latter change can be detected by the voltage-controlled analysis unit especially if the reference electrode is connected to the voltage-controlled analysis unit in an electrically conductive manner.

It was found that it is especially favorable if the receptor layer comprises a support and an analyte-binding layer. The analyte-binding layer may interact with both the analyte to be detected and the support. An interaction of the analyte-binding layer with an analyte preferably leads to a change in the work function of the support and consequently to the detectable change in capacitance already described above. It is especially advantageous in this connection if the analyte-binding layer is a self-assembling monolayer (self-assembling monolayer, SAM). This SAM forms the layer that interacts with the analyte to be detected and to which the analyte can bind preferably reversibly (on which it can preferably be deposited).

A self-assembling monolayer (SAM) is typically a layer whose thickness corresponds to one molecule of the material forming the layer. The material forming the layer is usually an organic compound. The molecules of a SAM are arranged spontaneously by adsorption on a surface and are oriented in relation to one another in a more or less ordered manner due to interaction with one another. The support of the receptor layer forms according to the present invention the surface on which the SAM is arranged and oriented. The support and the analyte-binding layer, i.e, the SAM, are preferably bound covalently to one another.

The gas sensor according to the present invention is characterized, furthermore, especially advantageously in that the receptor layer consists of a support, on the surface of which a SAM is formed, whose molecules correspond to the formula $R^1R^2$—X. While the coupling group is used to bind the molecules of the SAM and to arrange them on the support, the spacer $R^2$ is used to maintain the molecules in a certain order among one another. X designates in this connection the reactive group of the molecule $R^1$—$R^2$—X. Analytes to be detected can interact with this reactive group. Just as the spacer as well, the reactive group may, moreover, affect the arrangement of the molecules of the SAM.

A special advantage according to the present invention is that X may be an organic or organometallic group with at least one delocalized π system. Relatively inert volatile organic compounds, e.g., benzene, can, in particular, also interact with the SAM in this manner.

A delocalized π system is typically defined here as molecular orbitals that extend over a plurality of C atoms and in which the electrons can move relatively freely. Mesomeric effects are characteristic of delocalized π systems. A mesomeric effect is the influencing of the electron distribution in such a system by atoms that attract the π binding electrons to themselves (electron-attracting effect, –M effect) or provide π binding electrons (electron pushing effect, +M effect).

This π system may interact, for example, with a delocalized π system of a corresponding analyte. The analyte may be added to the reactive group X and bring about a shift of the π electrons. The pushing of the π electrons leads to a change in the dipole moment of the molecules involved and consequently to a desired and measurable change in the work function.

The addition of the analyte to the X group preferably takes place via intermolecular interactions, for example, by the action of Van der Waals forces or by hydrogen bridges. It is conceivable that the intermolecular interaction between the analyte molecules and the reactive group X leads to stabilization of a complex. The pushing of the π electrons especially in the X group or the change in the dipole moments of the participating molecules can be transmitted to the support by means of electron-pushing or electron-attracting effects by substituents on the X group via the spacer $R^2$ and the coupling group $R^1$, as a result of which there will ultimately be a change in the work function.

It is favorable in this connection if $R^2$ is a spacer, which is selected from the group containing alkane, alkene, alkyne, heteroalkane, heteroalkene, heteroalkyne, substituted alkanes, substituted alkenes, substituted alkynes, substituted heteroalkanes, substituted heteroalkenes, substituted heteroalkynes, ethers or amines. The distance between the support or the coupling group and the reactive group can be determined by means of such a spacer. It is therefore advantageous if the spacer is a linear molecule or a linear molecular group. For example, the spacer may have a linear atomic chain as a backbone, which consists of carbon atoms or a mixture of carbon, oxygen and nitrogen atoms. The atoms of the linear atomic chain may be connected to one another by single, double and/or triple bonds. Thus, the spacer may be, for example, an alkane, alkene, alkyne or even a heteroalkane, heteroalkene or heteroalkyne. In addition, substituents, which support, for example, the transmission of the dipole change from the reactive group X to the coupling group $R^1$, may be bound to the backbone. These substituents may lead to interactions between adjacent spacers. The order and stability of the SAM can also be supported and influenced in this manner by means of the spacer. It may therefore also be advantageous if the spacer is a substituted alkane, substituted alkene, substituted alkyne or even a substituted heteroalkane, substituted heteroalkene or substituted heteroalkyne.

It was found that it is, in addition, advantageous if $R^1$ is a coupling group that is selected from the group containing sulfide, disulfide, sulfinyl, sulfino, sulfo, carbonothiol, thiocyanate, isothiocyanate, preferably sulfide or thiosulfate. The individual molecules of the SAM can interact with the metal atoms arranged on the surface of the support by means of such a coupling group and form a covalent bond. It is especially advantageous if the coupling group has at least one sulfur atom, which brings about the binding of the coupling group $R^1$ to the surface of the support. Each coupling group $R^1$ preferably forms a bond with exactly one surface atom of the support. It is thus seen that it is favorable if the support is a layer consisting of metal, the metal being selected from the group containing gold, platinum, palladium, silver and copper.

In any case, it is favorable in a gas sensor according to the present invention if the support is a layer consisting of gold or comprised of gold. SAMs can be arranged especially well on a gold layer. Such a support is therefore well suited for being coated with a SAM as an analyte-binding layer. In addition, gold can interact especially well with sulfur compounds. A gold layer can, in addition, be prepared with high purity and is especially insensitive to oxidation.

In addition, it is advantageous if the coupling group $R^1$ is bound covalently to the spacer $R^2$ and to the support. The coupling group $R^1$ can control in this manner the arrangement of the individual molecules on the support and anchor the SAM molecules in their positions on the support.

It is favorable for such a binding of the SAM molecules if the coupling group $R^1$ forms at least one sulfur bridge between the spacer and the support. A coupling of the SAM molecules via a sulfur bridge is advantageous especially if the support consists of gold. It is thus favorable if $R^2$ is selected from the group containing sulfide or thiosulfate. Thiol groups, in particular, have a high affinity for noble metals, especially gold. It is therefore especially advantageous if $R^1$ is a sulfide radical.

It is advantageous in another aspect that $R^2$ is selected from the group containing alkanes, alkenes, alkynes, substituted alkanes, substituted alkenes, substituted alkynes, ethers, amines, wherein the substituents of the substituted alkanes, alkenes or alkynes are selected from the group containing hydrogen, alkyl or aryl. It is also conceivable as an alternative that $R^2$ is selected from the group containing heteroalkenes, heteroalkynes, substituted heteroalkenes and substituted heteroalkynes.

It is favorable in any case if the length of the atomic chain that forms the backbone of the spacer $R^2$ is shorter than or equal to 40 atoms. It is preferable in this respect if the length of the atomic chain equals 5, 6, 7, 8, 9, 10, 11, 12, 13, 14 or 15 atoms, especially preferably 6, 7, 8, 9, 10, 11 or 12 atoms and especially preferably 6, 7, 8, 9 or 10 atoms.

It is thus seen that it is favorable if $R^2$ is a linear molecular group corresponding to the formula $(Y)_n$, in which n∈ $\{0, \ldots, 40\}_{\mathbb{Z}}$, wherein each Y is selected, independently from the other Y values of the respective $R^2$, from the group containing $CH_2$, CH, C, $CR^3$, O, N, $NR^3$, and wherein $R^3$ is selected from the group containing H, alkane, alkene, alkyne or an aromatic compound. Y designates here the elements or radicals of $R^3$, which form the linear atomic chain of the spacer backbone. It is thus conceivable, for example, that $R^2$ is a molecular group corresponding to the formula $(CH_2)_4(CH)_2(CH_2)_6$, which would be represented as $(Y)_{12}$, wherein Y would be selected in this case from among $CH_2$ and CH. A molecule of a corresponding SAM could be represented in this case according to the formula as $R^1$—$R^2$—X correspondingly as $R^1$—$(Y)_{12}$—X, wherein Y is $CH_2$ or CH, or as $R^1$—$(CH_2)_4(CH)_2(CH_2)_6$—X. It is apparent that this example is only used to explain the notation of the formula and does not in any way represent a limitation of the present invention. The set of possible and conceivable combinations for the radicals Y of the spacer $R^2$ is rather obtained from the set of different conceivable lengths of the chains formed by Y and from the selection of the conceivable radicals for Y, which were described above. It is especially preferred in this connection if $n \in \{5, \ldots, 15\}_z$, preferably $n \in \{6, \ldots, 10\}_z$. The formula

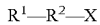

of the molecules of the SAM can therefore also be represented in a preferred embodiment variant as

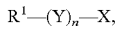

in which $n \in \{0, \ldots, 20\}_z$, preferably $n \in \{5, \ldots, 15\}_z$, and especially preferably $n \in \{6, \ldots, 10\}_z$.

It is advantageous if $R^2$ is selected such that the spacers of adjacent molecules interact with one another by Van der Waals forces. The spacers can stabilize the SAMs especially well in this manner. In particular, the spacers can contribute in this manner to the reactive groups X of adjacent molecules being oriented in a favorable position in relation to one another, so that analytes to be detected can effectively interact with the SAM. For example, the reactive groups X may be oriented such that a corresponding analyte to be detected is intercalated between the reactive groups X of two adjacent molecules, and this intercalation brings about a change in the dipole moment of the molecules of the SAM. It is also conceivable in this connection that the spacers of adjacent molecules are bound covalently to one another. A covalent binding may be formed both along the entire chain of $R^2$ and between individual segments of the chain of $R^2$.

It is seen, on the whole, that the SAM may have a great variety of different combinations of the groups $R^1$ and $R^2$. In an especially preferred embodiment variant, $R^1$ is a sulfur-containing radical, e.g., a sulfide group, and $R^2$ is an alkane, alkene or alkyne, wherein the alkane, alkene or alkyne may have as an option one or more substituents and a length of up to 40 atoms, preferably 6 to 12 atoms, and especially preferably 6 to 10 atoms, along its longest chain. Thus, $R^2$ is preferably a radical corresponding to $(Y)_n$. It is especially preferred in this respect if $R^1$—$R_2$ is an alkane thiol, alkene thiol or alkyne thiol, optionally a substituted alkane thiol, alkene thiol or alkyne thiol, with a corresponding chain length. Such thiol compounds (thio alcohols) may generally also be called mercaptan compounds. In other words, in an especially preferred embodiment, the starting molecules of the SAM correspond, for example, to the formula

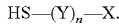

It is favorable in all these conceivable variants for $R^1$ and $R^2$ or $R^1$—$R^2$ if the delocalized π system of the reactive group X according to the present invention is selected from the group containing conjugated π systems with carbon atoms as binding centers, cyclically conjugated π systems, π systems of radicals with a plurality of cyclically conjugated π systems. The cyclically conjugated π systems are bound via at least one linker in radicals that have a plurality of such systems. The cyclically conjugated π systems are preferably planar cyclic compounds, i.e., consequently planar, cyclically conjugated π systems. The planar, cyclically conjugated π systems of aromatic or heteroaromatic systems are especially preferred. If the reactive group X is a radical that has a plurality of such cyclic planar π systems, which are bound via a linker, the linker is preferably selected from the group containing C, azo group, linear conjugated π system or a metallic central ion, which coordinates the cyclic conjugated π systems as a metal complex. It is also favorable in this connection if the entire group X is a planar group. In any case, X may have both electron-attracting and electron-pushing substituents. In a preferred embodiment variant, X is an aromatic or heteroaromatic radical or a radical containing at least one aromatic or heteroaromatic group. It is also conceivable in this connection, in particular, that X is a substituted aromatic or heteroaromatic radical.

X may be an aromatic or heteroaromatic radical with at least one electron-attracting substituent. A corresponding electron-attracting substituent may preferably be selected from the group containing $COOR^4$, COOH, CHO, C=(O)$R^4$, CN, CH=CH—COOH, $NO_2$, $SO_3H$, $CF_3$, especially preferably from the group containing $CF_3$, CN, $NO_2$, wherein $R^4$ is selected from the group containing H, aryl, alkyl, heteroaryl and heteroalkyl.

It is also conceivable that X is an aromatic or heteroaromatic radical containing at least one electron-pushing substituent. A corresponding electron-pushing substituent may preferably be selected from the group containing $NH_2$, $NR^5_2$, $OCH_3$, $CH_3$, OH, OR, NHC=(O)$R^5$, OC=(O)$R^5$, aryl, Br, Cl, I, F, especially preferably selected from the group containing $CH_3$, $OCH_3$, $NH_2$, wherein $R^5$ is selected from the group containing H, aryl, alkyl, heteroaryl, heteroalkyl and halide.

An aromatic or heteroaromatic radical according to the present invention may be selected, for example, from the group containing furane, pyrrole, thiophene, imidazole, pyrazole, oxazole, isoxazole, thiazole, benzofurane, isobenzofurane, indole, isoindole, benzothiophene, benzimidazole, purine, indazole, benzoxazole, benzisoxazole, benzothiazole, benzene, pyridine, pyrazine, pyrimidine, pyridazine, naphthalene, anthracene, quinoline, isoquinoline, chinoxaline, acridine, quinazoline, cinnoline, cinnoline and the like. Each of these radicals may have one or more of the above-described electron-attracting or electron-pushing substituents.

If the π system of the radical X is a linear, conjugated π system, the X may be a polymethine radical or a carbonyl radical.

In an especially simple embodiment, X may be, for example, a phenyl radical. The X may be an anthracene, naphthalene, furane, indole, pyridine, pyrimidine or pyrrole radical. As an alternative the X may be a substituted phenyl radical, wherein the substituent is selected from the group containing $COOR^4$, COOH, CHO, C=(O)$R^4$, CN, CH=CH—COOH, $NO_2$, $SO_3H$, $CF_3$, especially preferably from the group containing H, aryl, alkyl, heteroaryl and heteroalkyl. This is especially favorable if $R^1$ is a thiole group and $R^2$ is a radical corresponding to $(Y)_n$ with $n \in \{0, \ldots, 40\}_z$, $n \in \{5, \ldots, 15\}_z$, especially preferably $n \in \{6, \ldots, 10\}_z$. The molecules of the SAM may therefore correspond to the formula

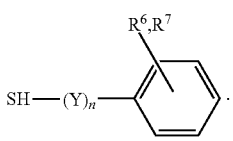

$R^6$ is preferably hydrogen or one or more electron-pushing radicals from the group containing $NH_2$, $NR^5{}_2$, $OCH_3$, $CH_3$, OH, OR, $NHC=(O)R^5$, $OC=(O)R^5$, aryl, Br, Cl, I, F, especially preferably from the group containing $CH_3$, $OCH_3$, wherein $R^5$ is selected from the group containing H, aryl, alkyl, heteroaryl, heteroalkyl and halide.

$R^7$ is preferably hydrogen or an electron-attracting radical from the group containing $COOR^4$, COOH, CHO, COW, CN, $CH=CH-COOH$, $NO_2$, $SO_3H$, $CF_3$, especially from the group containing $CF_3$, CN, $NO_2$, wherein $R^4$ is selected from the group containing H, aryl, alkyl, heteroaryl and heteroalkyl.

$(Y)_n$ is preferably defined as above, wherein n is preferably $n \in \{0, \ldots, 40\}_z$, especially preferably $n \in \{5, \ldots, 15\}_z$, and especially preferably $n \in \{6, \ldots, 10\}_z$. It is advantageous in this connection if Y is selected from the group containing alkane, alkene, alkyne, substituted alkane, substituted alkene, substituted alkyne, ether or amine, wherein the substituents are selected from the group containing hydrogen, alkyl or an aromatic, especially preferably hydrogen or alkyl groups. An especially preferred embodiment of the SAM molecules therefore corresponds to the formula

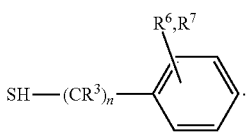

In another embodiment the X may be a polymethine radical, i.e., a conjugated polyene, in which an electron acceptor is linked to an electron donor via an odd-numbered chain of methine groups. For example, X may be a group corresponding to the formula,

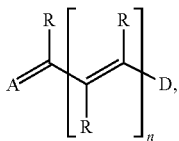

wherein A is an electron acceptor, D is an electron donor, R is hydrogen or alkyl and n is an integer or zero. Here, X is preferably bound covalently to the spacer $R^2$ via one of the radicals R. This is especially favorable if $R^1$ is a thiol group and $R^2$ is a radical corresponding to $(Y)_n$ with $n \in \{0, \ldots, 40\}_z$, preferably $n \in \{5, \ldots, 15\}_z$, and especially preferably $n \in \{6, \ldots, 10\}_z$. The molecules of the SAM can therefore correspond to the formula

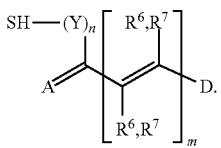

$R^6$ and D are preferably hydrogen, alkyl or an electron-pushing radical from the group containing $NR^5{}_2$, $OCH_3$, $CH_3$, $OR^5$, $NHC=(O)R^5$, $OC=(O)R^5$, aryl, Br, Cl, I, F, especially preferably selected from the group containing $CH_3$, $OCH_3$, $NH_2$, wherein $R^5$ is selected from the group containing H, aryl, alkyl, heteroaryl, heteroalkyl and halide.

$R^7$ and A are preferably hydrogen, alkyl or an electron-attracting radical from the group containing $COOR^4$, COOH, CHO, $C=O$, CN, $CH=CH-COOH$, $NO_2$, $SO_3H$, $CF_3$, especially preferably from the group containing $CF_3$, CN, $NO_2$, wherein $R^4$ is selected from the group containing H, aryl, alkyl, heteroaryl and heteroalkyl.

$R^6$ and $R^7$ are, independently from each other, especially preferably hydrogen or an alkyl radical.

m is an integer or zero.

$(Y)_n$ is preferably defined as above, wherein n is preferably $n \in \{0, \ldots, 20\}_z$, especially preferably $n \in \{5, \ldots, 15\}_z$, and especially preferably $n \in \{6, \ldots, 10\}_z$. It is advantageous in this connection if Y is selected from the group containing alkane, alkene, alkyne, substituted alkane, substituted alkene, substituted alkyne, ether or amine, wherein the substituents are selected from the group containing hydrogen, alkyne or aryl, especially preferably hydrogen or alkyl. An especially preferred embodiment of the SAM molecules therefore corresponds to the formula

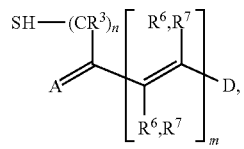

in which $R^3$, $R^6$ and $R^7$ are defined as above.

In another embodiment, X may be the dye parent substance of a nitro dye, i.e., an aromatic ring, to which at least one nitro group is bound. For example, X may be a group corresponding to the formula

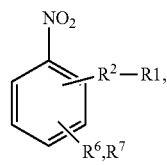

wherein $R^6$, $R^7$ may be hydrogen or a nitrogen-containing organic radical, which is bound to the nitrobenzyl radical via a nitrogen atom, and wherein X is preferably bound to the spacer $R^2$ covalently via this radical $R^6$ or $R^7$ or an additional carbon atom of the ring. This is especially favorable if $R^1$ is a thiol group and $R^2$ is a radical corresponding to $(Y)_n$ with $n \in \{0, \ldots, 40\}_z$, preferably $n \in \{5, \ldots, 15\}_z$ and especially preferably $n \in \{6, \ldots, 10\}_z$. The molecules of the SAM may therefore correspond to the formula

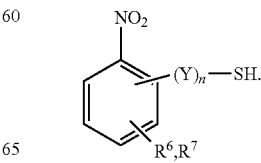

$R^6$ is preferably hydrogen or an electron-pushing radical from the group containing $NR^5_2$, $OCH_3$, $CH_3$, $OH$, $OR$, $NHC=(O)R^5$, $OC=(O)R^5$, aryl, Br, Cl, I, F, especially preferably selected from the group containing $CH_3$, $OCH_3$, $NH_2$, wherein $R^5$ is selected from the group containing H, aryl, alkyl, heteroaryl, heteroalkyl and halide.

$R^7$ is preferably hydrogen or an electron-attracting radical from the group containing $COOR^4$, COOH, CHO, $C(O)R^4$, CN, CH=CH—COOH, $NO_2$, $SO_3H$, $CF_3$, especially preferably from the group containing $CF_3$, CN, $NO_2$, wherein $R^4$ is selected from the group containing H, aryl, alkyl, heteroaryl and heteroalkyl.

$R^6$ and $R^7$ are, independently from one another, especially preferably either hydrogen or a radical corresponding to $NR^5R^4$, $NO_2$, $NHC=(O)R^5$, $NR^5_2$ or $NH_2$, in which $R^5$, $R^4$ are defined as above.

$(Y)_n$ is preferably as defined above, n preferably being $n \in \{0, \ldots, 40\}_z$, especially preferably $n \in \{5, \ldots, 15\}_z$, and especially preferably $n \in \{6, \ldots, 10\}_z$. It is advantageous in this connection if Y is selected from the group containing alkane, alkene, alkyne, substituted alkane, substituted alkene, substituted alkyne, ether or amine, wherein the substituents are selected from the group containing hydrogen, alkyl or aryl, especially preferably hydrogen or alkyl. An especially preferable embodiment of the SAM molecules therefore corresponds to the formula

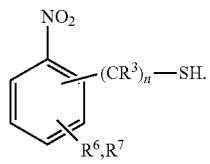

It is also conceivable in yet another embodiment that X is the dye parent substance of an azo dye, in which at least two aromatic rings are linked via an azo group. For example, X may be a group corresponding to the formula

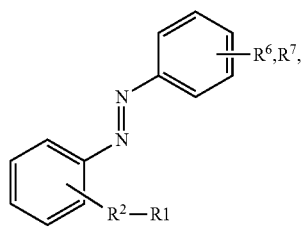

in which $R^6$ and $R^7$ may each be, independently from one another, hydrogen, aryl, alkyl or a nitrogen-containing organic radical. This is especially favorable if $R^1$ is a thiol group and $R^2$ is a radical corresponding to $(Y)_n$ with $n \in \{0, \ldots, 40\}_z$, preferably $n \in \{5, \ldots, 15\}_z$, and especially preferably $n \in \{6, 10\}_z$. The molecules of the SAM may therefore correspond to the formula

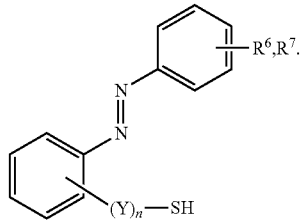

$R^6$ is preferably hydrogen or an electron-pushing radical from the group containing $NR^5_2$, $OCH_3$, $CH_3$, $OH$, $OR$, $NHC=(O)R^5$, $OC=(O)R^5$, aryl, Br, Cl, I, F, especially preferably selected from the group containing $CH_3$, $OCH_3$, $NH_2$, wherein $R^5$ is selected from the group containing H, aryl, alkyl, heteroaryl, heteroalkyl and halide.

$R^7$ is, independently from $R^6$, preferably hydrogen or an electron-attracting radical from the group containing $COOR^4$, COOH, CHO, $C(O)R^4$, CN, CH=CH—COOH, $NO^2$, $SO_3H$, $CF_3$, especially preferably from the group containing $CF_3$, CN, $NO_2$, wherein $R^4$ is selected from the group containing H, aryl, alkyl, heteroaryl and heteroalkyl.

$R^6$ and $R^7$ are, independently from one another, especially preferably either hydrogen, aryl, alkyl or a radical corresponding to $NR^5R^4$, $NO_2$, $NHC=(O)R^5$, $NR^5_2$ or $NH_2$, with $R^5$, $R^4$ as defined above.

$(Y)_n$ is preferably as defined above, wherein n is preferably $n \in \{0, \ldots, 40\}_z$, especially preferably $n \in \{5, \ldots, 15\}_z$, and especially preferably $n \in \{6, \ldots, 10\}_z$. It is advantageous in this connection if Y is selected from the group containing alkane, alkene, alkyne, substituted alkane, substituted alkene, substituted alkyne, ether or amine, wherein the substituents are selected from the group containing hydrogen, alkyl and aryl, especially preferably hydrogen and alkyl. An especially preferred embodiment of the SAM molecules therefore corresponds to the formula

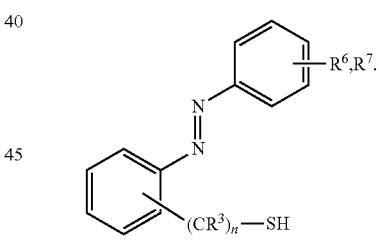

It is conceivable in another embodiment that the reactive group X is a dye parent substance of a carbonyl dye. At least two carbonyl groups are conjugated via one or more π bonds in such a radical. For example, X may be a group corresponding to the formula,

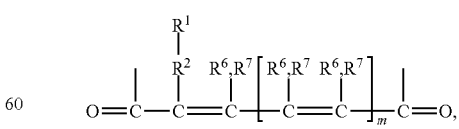

wherein $R^6$ and $R^7$ may each be, independently from one another, hydrogen, aryl, alkyl or a nitrogen-containing organic radical. m is an integer or zero. This is especially favorable if $R^1$ is a thiol group and $R^2$ is a radical corresponding to $(Y)_n$ with $n \in \{0, \ldots, 40\}_z$, preferably $n \in$ $\{5, \ldots, 15\}_z$, and especially favorably $n \in \{6, \ldots, 10\}_z$. The molecules of the SAM may therefore correspond to the formula

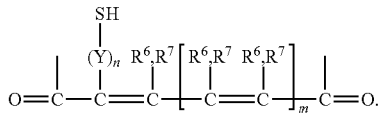

Here, $R^6$ is especially favorably hydrogen or an electron-pushing radical from the group containing $NR^5_2$, $OCH_3$, $CH_3$, OH, OR, $NHC=(O)R^5$, $OC=(O)R^5$, aryl, Br, Cl, I, F, especially preferably selected from the group containing $CH_3$, $OCH_3$, $NH_2$, wherein $R^5$ is selected from the group containing H, aryl, alkyl, heteroaryl, heteroalkyl and halide. $R^7$ is, independently from $R^6$, preferably hydrogen or an electron-attracting radical from the group containing $COOR^4$, COOH, CHO, $C(O)R_4$, CN, CH=CH—COOH, $NO_2$, $SO_3H$, $CF_3$, especially from the group containing $CF_3$, CN, $NO_2$, wherein $R^4$ is selected from the group containing H, aryl, alkyl, heteroaryl and heteroalkyl.

$R_6$ and $R^7$ are, independently from each other, especially preferably either hydrogen or aryl. $(Y)_n$ is preferably defined as above, wherein n is preferably $n \in \{0, \ldots, 40\}_z$, especially preferably $n \in \{5, \ldots, 15\}_z$ and especially preferably $n \in \{6, \ldots, 10\}_z$. It is advantageous in this connection if Y is selected from the group containing alkane, alkene, alkyne, substituted alkane, substituted alkene, substituted alkyne, ether or amine, wherein the substituents are selected from the group that contains hydrogen, alkyl or aryl, especially preferably hydrogen or alkyl groups. An especially preferred embodiment of the SAM molecules therefore corresponds to the formula

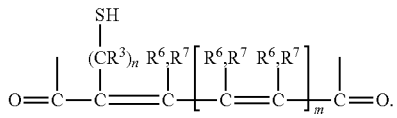

It is conceivable in another embodiment that the reactive group X is a dye parent substance of a triarylcarbenium dye. Such dye parent substances are derivatives of triphenylmethane. For example, X may contain a group corresponding to the formula

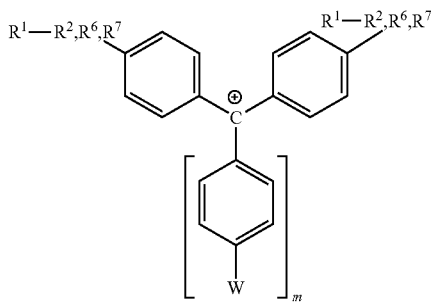

wherein $R^6$ and $R^7$ may be each, independently from one another, hydrogen, aryl, alkyl or a nitrogen-containing organic radical. m is selected from 0 or 1. W is hydrogen or a nitrogen-containing organic radical. This is especially favorable if $R^1$ is a thiol group and $R^2$ is a radical corresponding to $(Y)_n$ with $n \in \{0, \ldots, 40\}_z$, preferably $n \in \{5, \ldots, 15\}_z$ and especially preferably $n \in \{6, \ldots, 10\}_z$. The molecules of the SAM may therefore correspond to the formula

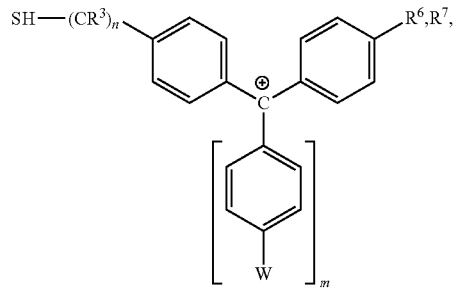

$R^6$ is preferably hydrogen or an electron-pushing radical from the group containing $NR^5_2$, $OCH_3$, $CH_3$, OH, OR, $NHC=(O)R^5$, $OC=(O)R^5$, aryl, Br, Cl, I, F, especially preferably selected from the group containing $CH_3$, $OCH_3$, $NH_2$, wherein $R^5$ is selected from the group containing H, aryl, alkyl, heteroaryl, heteroalkyl and halide.

$R^7$ is, independently from $R^6$, preferably hydrogen or an electron-pushing radical from the group containing $COOR^4$, COOH, CHO, $C(O)R^4$, CN, CH=CH—COOH, $NO_2$, $SO_3H$, $CF_3$, especially preferably from the group containing $CF_3$, CN, $NO_2$, wherein $R^4$ is selected from the group containing H, aryl, alkyl, heteroaryl, heteroalkyl.

$R^6$ and $R^7$ are especially preferably, independently from one another, either a nitrogen-containing organic radical according to the formula $NR^4R^5$, oxygen or a hydroxyl group, with $R^4$ and $R^5$ as defined above.

$(Y)_n$ is preferably as defined above, wherein n is preferably $n \in \{0, \ldots, 40\}_z$, especially preferably $n \in \{5, \ldots, 15\}_z$ and especially preferably $n \in \{6, \ldots, 10\}_z$. It is advantageous in this connection if Y is selected from the group containing alkane, alkene, alkyne, substituted alkane, substituted alkene, substituted alkyne, ether or amine, wherein the substituents are selected from the group that contains hydrogen, alkyl or aryl, especially preferably hydrogen or alkyl. An especially preferred embodiment of the SAM molecules therefore corresponds to the formula

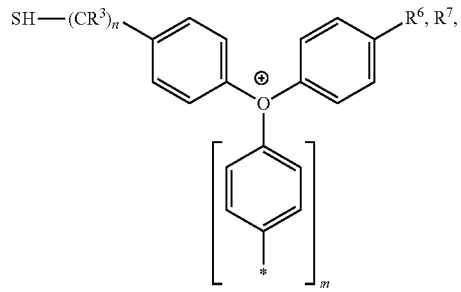

It is conceivable in another embodiment that the reactive group X is the dye parent substance of an anthocyanidine dye. Such dye parent substances are hydroxylated derivatives of the flavylium ion. X may be, for example, a group corresponding to the formula

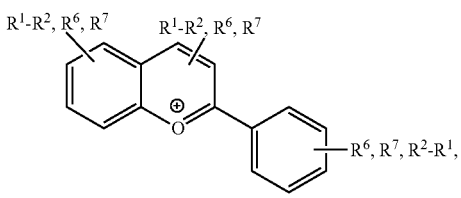

wherein $R^6$ and $R^7$ may be each, independently from one another, hydrogen or a hydroxyl radical. However, at least one radical $R^6$ or $R^7$ is a hydroxyl radical. This is especially favorable if $R^1$ is a thiol group and $R^2$ is a radical corresponding to $(Y)_n$, in which $n \in \{0, \ldots, 40\}_z$, preferably $n \in \{5, \ldots, 15\}_z$ and especially preferably $n \in \{6, \ldots, 10\}_z$. The molecules of the SAM may therefore correspond to one of the formulas

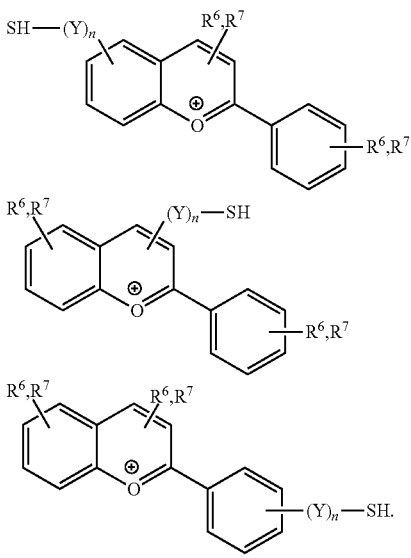

$R^6$ and $R^7$ are preferably hydrogen or an electron-pushing radical from the group containing $OCH_3$ or $OH$, especially preferably selected from the group containing $OCH_3$ and $OH$. Independently from one another, $R^6$ and $R^7$ are especially preferably either hydrogen or a hydroxyl radical.

$(Y)_n$ is preferably as defined above, wherein n is preferably $n \in \{0, \ldots, 40\}_z$, especially preferably $n \in \{5, \ldots, 15\}_z$ and especially preferably $n \in \{6, \ldots, 10\}_z$. It is advantageous in this connection if Y is selected from the group containing alkane, alkene, alkyne, substituted alkane, substituted alkene, substituted alkyne, ether or amine, wherein the substituents are selected from the group containing hydrogen, alkyl and aryl, especially preferably hydrogen and alkyl. An especially preferred embodiment of the SAM molecules therefore corresponds to the formula

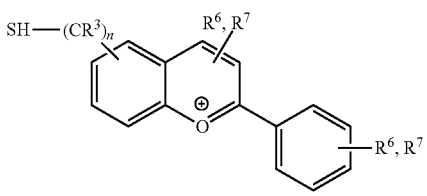

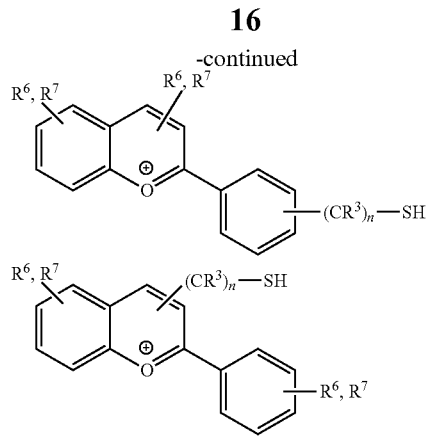

It is conceivable in another embodiment that the reactive group X is the dye parent substance of a metal complex dye, e.g., of a phthalocyanine-copper complex. For example, X may be a group corresponding to the formula

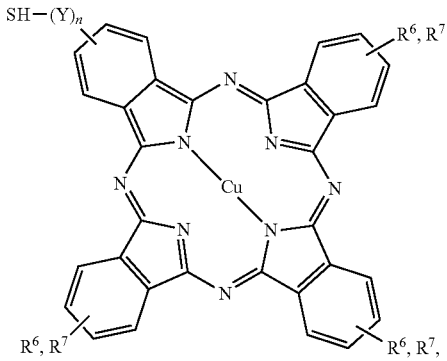

wherein $R^6$ and $R^7$ may be each, independently from one another, hydrogen or halogen. This is especially favorable if $R^1$ is a thiol group and $R^2$ is a radical corresponding to $(Y)_n$, in which $n \in \{0, \ldots, 40\}_z$, preferably $n \in \{5, \ldots, 15\}_z$ and especially preferably $n \in \{6, \ldots, 10\}_z$. The molecules of the SAM may therefore correspond to the formula

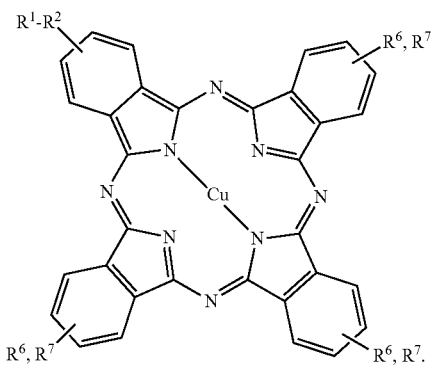

$R^6$ and $R^7$ are preferably hydrogen or halogen.
$R^6$ and $R^7$ are especially preferably hydrogen.
$(Y)_n$ is preferably defined as above, n preferably being $n \in \{0, \ldots, 40\}_z$, preferably $n \in \{5, \ldots, 15\}_z$ and especially preferably $n \in \{6, \ldots, 10\}_z$. It is advantageous in this connection if Y is selected from the group containing alkane, alkene, alkyne, substituted alkane, substituted alkene, substituted alkyne, ether or amine, wherein the substituents are selected from the group containing hydrogen, alkyl or aryl, preferably hydrogen and alkyl, especially preferably hydrogen groups. An especially preferred embodiment of the SAM molecules therefore corresponds to the formula

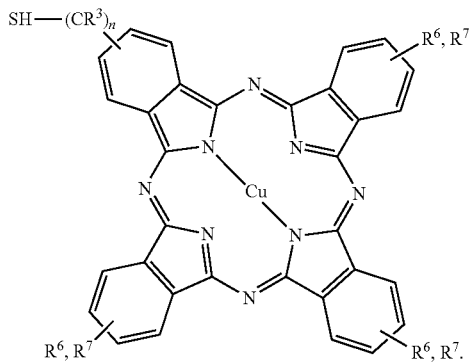

In other words, X is preferably selected from the group containing polyenes, nitro dyes, azo dyes, triphenylmethane derivatives, anthocyanidines, and phthalocyanine-metal complexes. It is also conceivable as an alternative that X is selected from the group containing aryl radicals, which are selected from the group containing phenyl, benzyl, pyridyl, anthraquinones, and naphthalene. It is especially advantageous in this connection that X is a radical containing at least one electron-attracting substituent, wherein the radical is selected from the group containing polymethine, aryl radicals, metal complexes, macrocyclic arenyl radicals and dendrimers, and wherein the substituent is preferably selected from the group containing $COOR^4$, COOH, CHO, $COR^4$, CN, CH=CH—COOH, $NO_2$, $SO_3H$, $CF_3$, especially preferably from the group containing $CF_3$, CN, $NO_2$, wherein $R^4$ is selected from the group containing H, aryl, alkyl, heteroaryl, and heteroalkyl. It may also be favorable that X is a radical containing at least one electron-pushing substituent, wherein the radical is selected from the group containing polymethine, aryl radicals, metal complexes, macrocyclic arenyl radicals and dendrimers, and wherein the substituent is preferably selected from the group containing $NR^5_2$, $OCH_3$, $CH_3$, OH, OR, NHC=(O)$R^5$, OC(O)$R^5$, aryl, Br, Cl, I, F and especially selected from the group containing $CH_3$ and $OCH_3$, wherein $R^5$ is selected from the group containing H, aryl, alkyl, heteroaryl, heteroalkyl and halide.

In a preferred embodiment of the present invention, the voltage-controlled analysis unit is a field-effect transistor, the field-effect transistor of the gas sensor according to the present invention being especially a capacitively controlled field-effect transistor (CCFET).

It is advantageous in this connection if the reference electrode is connected to the gate electrode of the field-effect transistor. A change in capacitance between the receptor layer and the reference electrode can bring about a change in the charge transport between the source and drain of the FET in this manner. This change in the flow of current can ultimately be used, for example, to trigger an alarm or the like.

In another aspect, the present invention provides a gas-measuring device with a gas sensor according to the present invention. In addition, the present invention provides for the use of a gas sensor according to the present invention for detecting volatile organic compounds, preferably benzene and/or benzene derivatives.

Further features, details and advantages of the present invention appear from the wording of the claims as well as from the following description of exemplary embodiments on the basis of the drawings.

The present invention is described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:
FIG. 3a is a view showing one of different examples for the reactive group X of the SAM molecules;
FIG. 3b is a view showing another of different examples for the reactive group X of the SAM molecules;
FIG. 3c is a view showing another of different examples for the reactive group X of the SAM molecules;
FIG. 3d is a view showing another of different examples for the reactive group X of the SAM molecules;
FIG. 3e is a view showing another of different examples for the reactive group X of the SAM molecules;
FIG. 3f is a view showing another of different examples for the reactive group X of the SAM molecules;
FIG. 3g is a view showing another of different examples for the reactive group X of the SAM molecules;
FIG. 4 is a schematic view of an analyte binding in a gas sensor according to the present invention.

DESCRIPTION OF THE PREFERRED EMBODIMENTS

Figure 1:
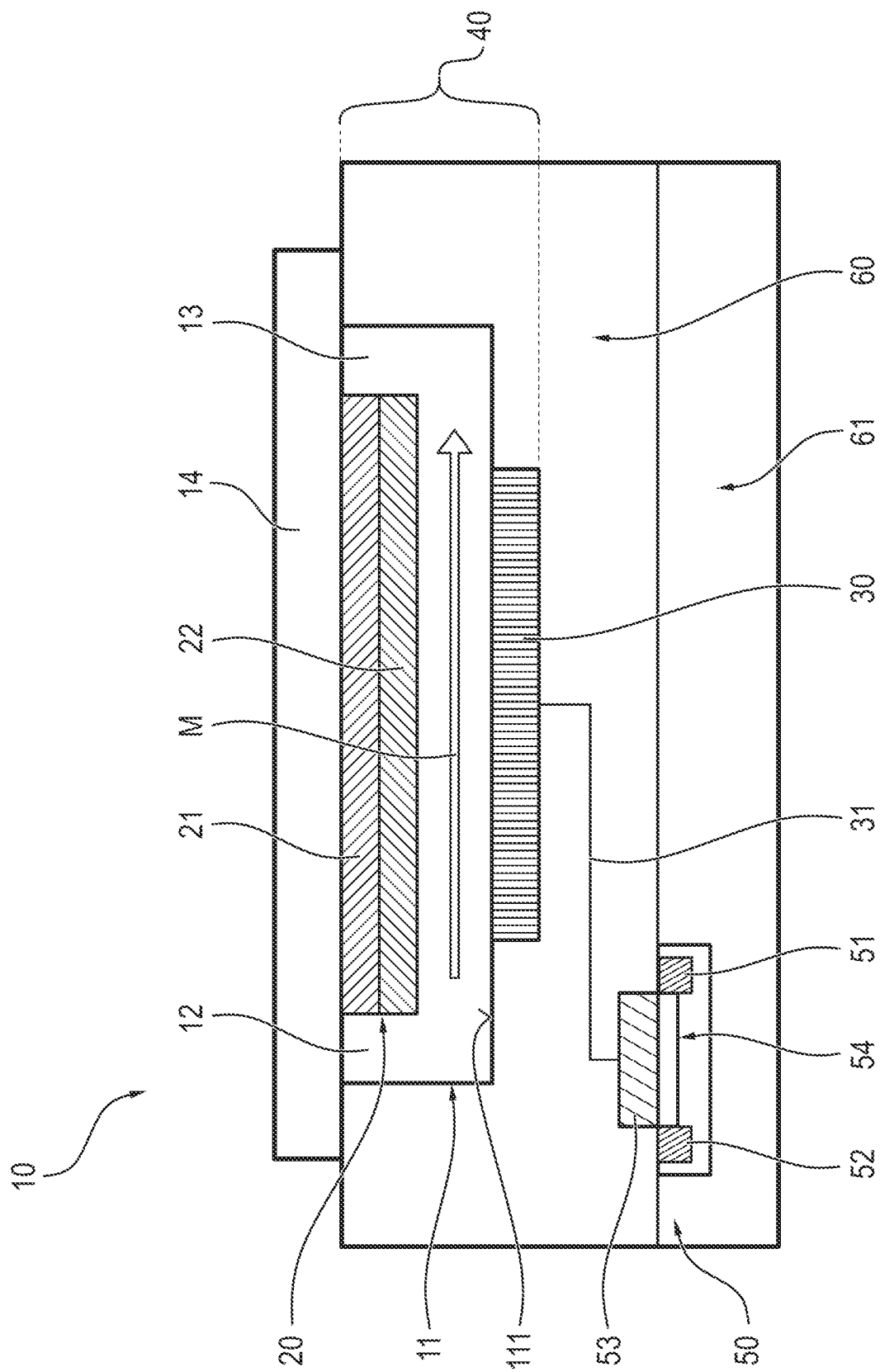
FIG. 1 is a schematic view of a gas sensor according to the present invention.

Referring to the drawings, the gas sensor 10 according to the present invention shown in FIG. 1 has a measuring channel 11, which is covered by a cover 14 and has a gas inlet 12 as well as a gas outlet 13. The volume of the measuring channel 11 is defined by the inner wall 111. A flow of gas to be measured M can flow through this volume to the gas outlet 13 and flow along the inner wall 111 in the process.

It is seen, in addition, in FIG. 1 that a receptor layer 20 is arranged in the interior of the measuring channel 11. The receptor layer 20 is applied to the cover 14. It comprises a support 21 and an analyte-binding layer 22. The receptor layer 20, especially the analyte-binding layer 22, forms here a part of the inner wall 111 of the measuring channel 11. A reference electrode 30 is arranged opposite the receptor layer 20. The receptor layer 20, the reference electrode 30 and the volume of the measuring channel 11 formed between the receptor layer 20 and the reference electrode 30 form a capacitor 40. It is seen in this respect that the reference electrode 30 is capacitively coupled with the receptor layer 20. The capacitance of this capacitor 40 can be changed by interactions of the analyte-binding layer 22 with an analyte contained in the measured gas flow M.

It is seen, furthermore, in FIG. 1 that the reference electrode 30 is connected to a voltage-controlled analysis unit 50 via an electrically conductive connection 31. The voltage-controlled analysis unit 50 is a field-effect transistor, namely, a CCFET, in the example being shown. The analysis unit 50 has in this respect a source electrode 51, a drain electrode 52 and a gate electrode 53. The reference electrode 30 is connected to the gate electrode 53. The gate electrode 53 is arranged above a channel 54, which connects the source electrode 51 and the drain electrode 52 to one another. The gate electrode 53 determines the charge flow, which takes place between the drain electrode and the source electrode 51, 52 through the channel 54 as a function of the capacitance of the capacitor 40.

The reference electrode 30 is embedded in an insulation layer 60 in the exemplary embodiment being shown. The analysis unit 50 is arranged between the insulation layer 60 and the substrate 61. The insulation layer 60 can help avoid or at least minimize false signals.

FIG. 1 shows in this respect a gas sensor 10, wherein the gas sensor 10 has a measuring channel 11 with a gas inlet 12 and with a gas outlet 13, at least one receptor layer 20, a reference electrode 30 and a voltage-controlled analysis unit 50, wherein the reference electrode 30 is capacitively coupled with the receptor layer 20, wherein the reference electrode 30 is connected to the analysis unit 50 in an electrically conductive manner, wherein the receptor layer 20 is formed in the measuring channel 11, wherein the measuring channel 11 forms a dielectric layer between the receptor layer 20 and the reference electrode 30, and wherein the receptor layer 20 has a support 21 and an analyte-binding layer 22.

Figure 2:
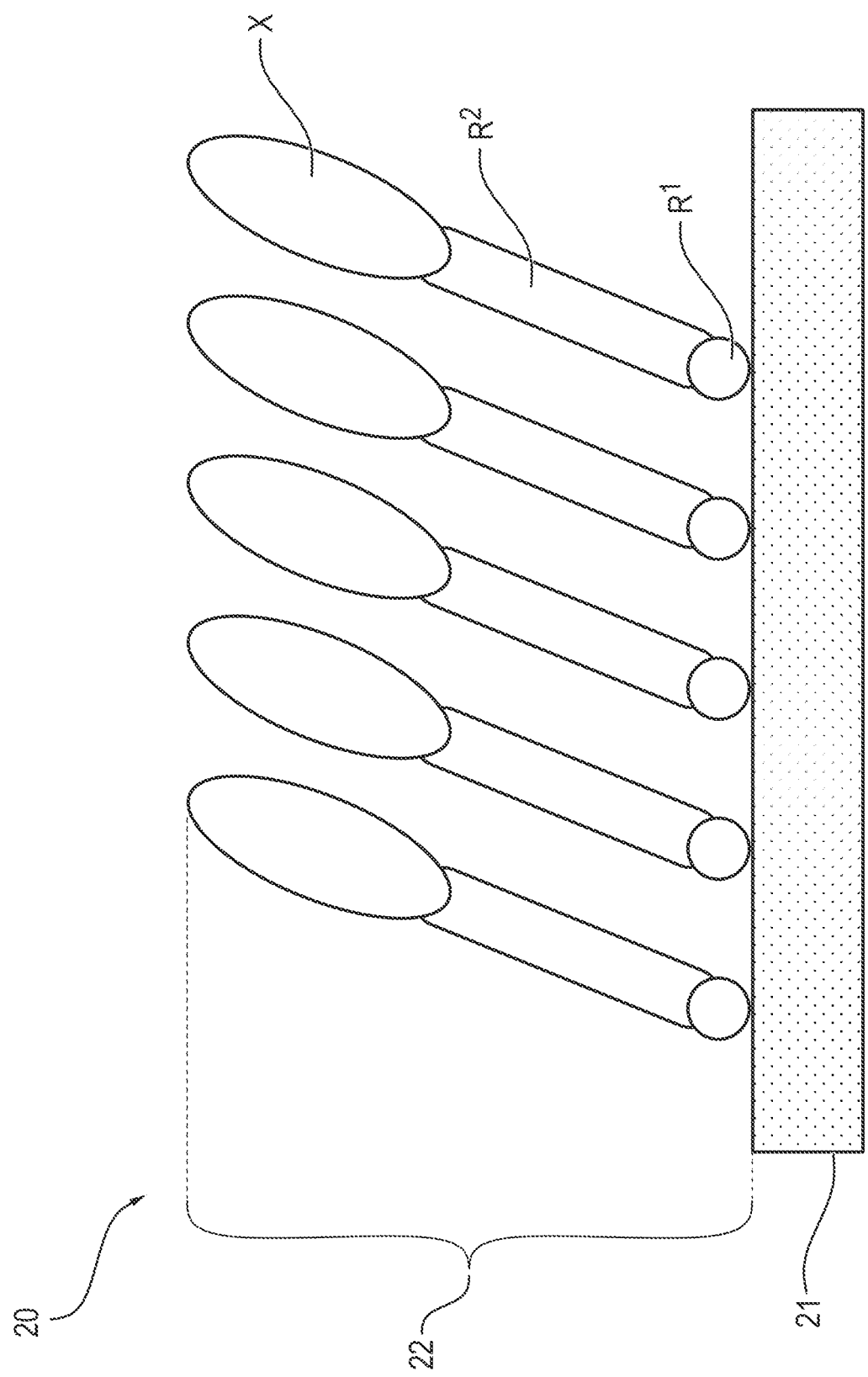
FIG. 2 is a schematic view of the receptor layer.

The analyte-binding layer 22 of such a gas sensor 10 is configured—as can be seen in FIG. 2—as a self-assembling monolayer (SAM). The molecules of this SAM correspond to the general formula $R^1$—$R^2$—X. It is seen that the molecules comprise three functional units, namely, the coupling group $R^1$, the spacer $R^2$ and the reactive group X. The molecules of the SAM, i.e., of the analyte-binding layer 22, are oriented on the support 21 in a synchronous orientation and parallel to one another. The molecules are always coupled to the support 21 via the coupling group $R^1$. The coupling group $R^1$ is selected from the group containing sulfide, disulfide and thiosulfate.

It is seen in FIG. 2 that the spacer $R^2$ determines the distance of the reactive group X from the coupling group $R^1$ and hence from the support 21. The spacer $R^2$ is selected from the group containing alkane, alkene, alkyne, heteroalkane, heteroalkene, heteroalkyne, substitute alkanes, substituted alkenes, substituted alkynes, substituted heteroalkanes, substituted heteroalkenes and substituted hetreroalkynes.

The reactive group X is an organic or organometallic group. To measure benzene, the group X has at least one delocalized π system. The support 21 is a layer consisting of metal, wherein the metal is selected from the group containing gold, platinum, palladium, silver and copper.

FIGS. 3a through 3h show different examples of embodiments of the reactive group X. It is obvious that the present invention is not limited to the molecules concretely shown here.

Corresponding to the exemplary embodiment shown in FIG. 3a, the reactive group X is a phenyl radical. The reactive group X is coupled with the radical $R^2$—$R^1$ via a covalent bond between the radical $R^2$ and one of the ring atoms of the phenyl radical. $R^6$ and $R^7$ are as described above. In an especially favorable exemplary embodiment (not shown in the figure) with such a reactive group X, the molecules of the SAM correspond to the formula

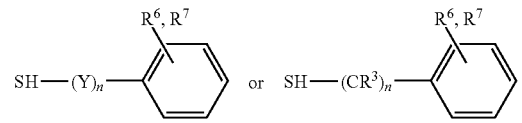

$R^6$, $R^7$, $R^3$, n and Y being defined as described above here as well.

According to the exemplary embodiment according to FIG. 3b, the reactive group X is a nitro dye, in which a nitro group is bound to an aromatic ring, namely, nitrophenyl. The aromatic ring may have an additional substituent according to the general formulas $NR^4R^5$. The reactive group X is coupled to the spacer $R^2$ via the ring. In an especially favorable exemplary embodiment (not shown) with such a reactive group X, the molecules of the SAM correspond to the formula

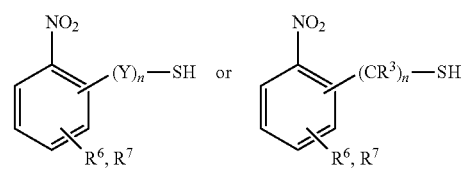

$R^6$, $R^7$, $R^3$, n and Y being defined as described above here as well.

The reactive group X is an azo dye in FIG. 3c. The reactive group X is coupled with the spacer $R^2$ via one of the rings. In an especially favorable exemplary embodiment (not shown) with such a reactive group X, the molecules of the SAM correspond to the formula

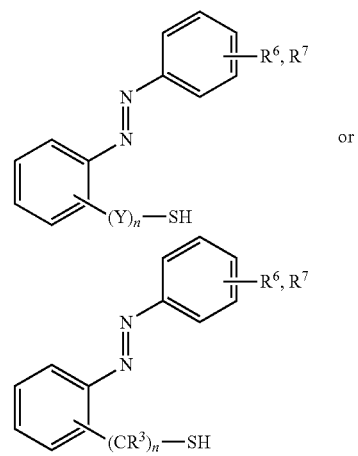

$R^6$, $R^7$, $R^3$, n and Y being defined as described above here as well.

Corresponding to the exemplary embodiment according to FIG. 3d, the reactive group X is a polymethine radical. The polymethine radical may have alkyl groups or hydrogen as substituents $R^6$, $R^7$. The reactive group X is coupled with the spacer $R^2$ via such a radical. In an especially favorable exemplary embodiment (not shown) with such a reactive group X, the molecules of the SAM correspond to the formula

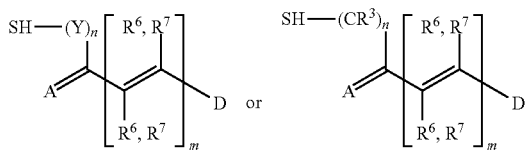

$R^6$, $R^7$, $R^3$, n, m and Y being defined as described above here as well.

In the exemplary embodiment shown in FIG. 3e, the reactive group X is a carbonyl dye. The reactive group X is coupled with the spacer $R^2$ via a radical $R^6$ or $R^7$. In an especially favorable exemplary embodiment (not shown) with such a reactive group X, the molecules of the SAM correspond to the formula

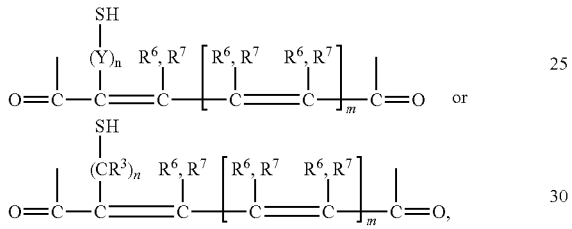

$R^6$, $R^7$, $R^3$, n, m and Y being defined as described above here as well.

In the exemplary embodiment shown in FIG. 3f, the reactive group X is a triarylcarbenium radical. The reactive group X is coupled with the spacer $R^2$ via one of the rings. In an especially favorable exemplary embodiment (not shown) with such a reactive group X, the molecules of the SAM correspond to the formula

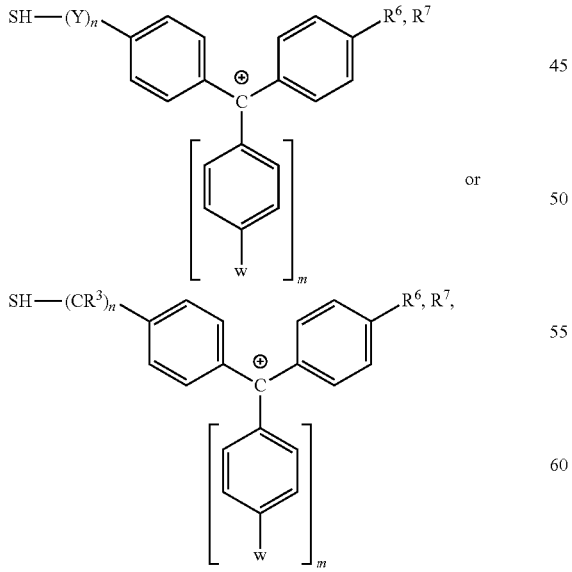

$R^6$, $R^7$, $R^3$, n, m, W and Y being defined as described above here as well.

The reactive group is an anthocyanine derivative in FIG. 3g. The reactive group X is coupled here to the spacer $R^2$ via one of the rings. In an especially favorable exemplary embodiment (not shown) with such a reactive group X, the molecules of the SAM correspond to one of the following formulas

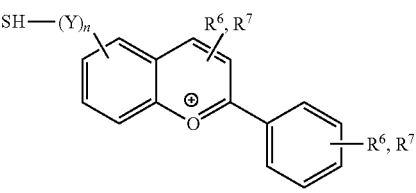

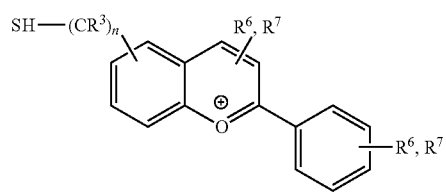

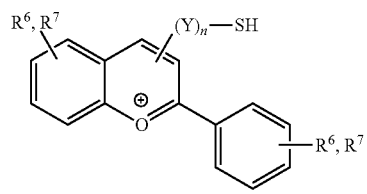

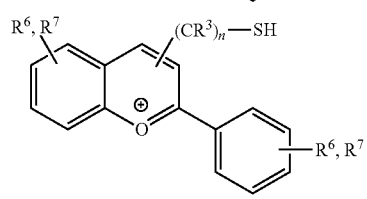

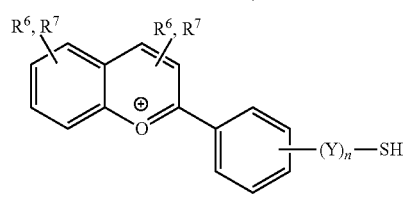

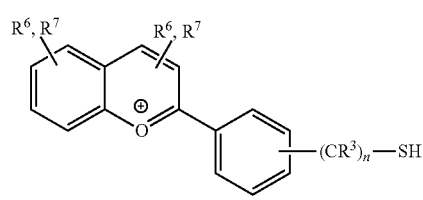

$R^6$, $R^7$, $R^3$, n and Y being defined as described above here as well.

Figure 3H:
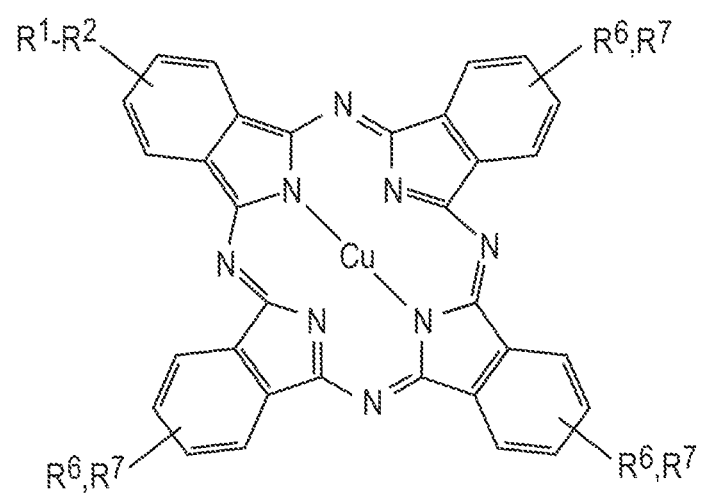
FIG. 3h is a view showing another of different examples for the reactive group X of the SAM molecules.

The reactive group is a metal complex, namely, copper phthalocyanidine, in FIG. 3h. The reactive group X is coupled with the spacer $R^2$ via one of the rings. In an especially favorable exemplary embodiment (not shown) with such a reactive group X, the molecules of the SAM correspond to the formula

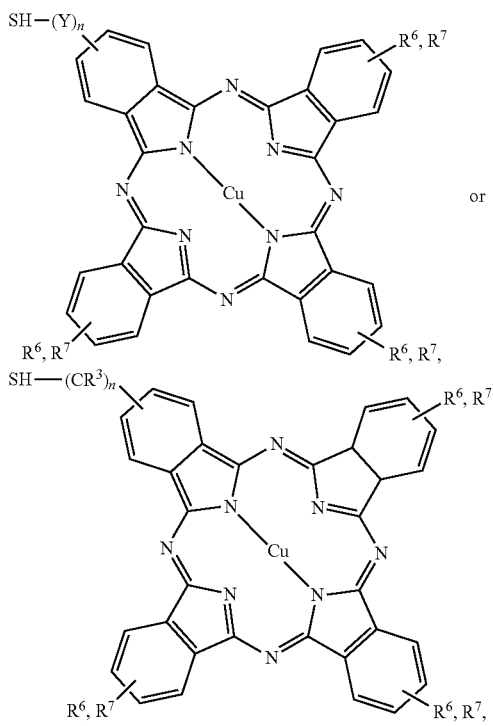

$R^6$, $R^7$, $R^3$, n and Y being defined as described above here as well.

It is seen in FIG. 4 how the steric arrangement of the molecules of the SAM, i.e., of the analyte-binding layer 22, may be. The molecules to the support 21 are coupled with the support 21 via a sulfur bridge. The coupling group $R^1$ is therefore a sulfide group. The hydrogen radicals of the thiol groups are split off during the coupling of the molecules, i.e., during the formation of the analyte-binding layer 22 due to the self-assembly of the molecules, and a covalent bond is formed between the sulfur atoms of the coupling group $R^1$ and the gold atoms of the support 21. The sulfur atoms of the coupling group $R^1$ are, in addition, bound covalently to the spacer $R^2$. The spacer $R^2$ consists of a linear chain of four methylene groups in the exemplary embodiment shown in FIG. 4. It should be noted here that the length of the spacer $R^2$ is between 6 and 12 atoms in especially favorable embodiments. The length of the spacer is reduced to only four methylene groups in FIG. 4 solely for reasons of clarity and for the sake of a clearer illustration. The reactive group X is bound to the methylene group of the spacer $R^2$, which is in terminal position relative to the coupling group $R^1$. The reactive group X is a phenyl ring in this exemplary embodiment. The phenyl ring carries a substituent $R^6$, $R^7$, namely, a nitro group. The SAM therefore consists of a layer of a substituted phenylalkyl mercaptan according to the formula

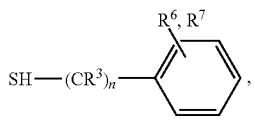

wherein $R^3$ is hydrogen, n=4, wherein the ring atoms of the phenyl radical in ortho and meta positions carry hydrogen each as a substituent $R^6$, $R^7$ and wherein the aromatic ring has a nitrogen group as a substituent in the para position.

It is further seen in the schematic view in FIG. 4 how an analyte A—benzene in the example being shown—can approach the analyte-binding layer 22 with the flow of gas to be measured. In the next step, the benzene molecules of the analyte A can add plane-parallel to the phenyl radicals of the reactive group X of the SAM. A charge shift can occur within the SAM in this manner. This shift is, in turn, detectable by means of the analysis unit as was described above.

Figure 5:
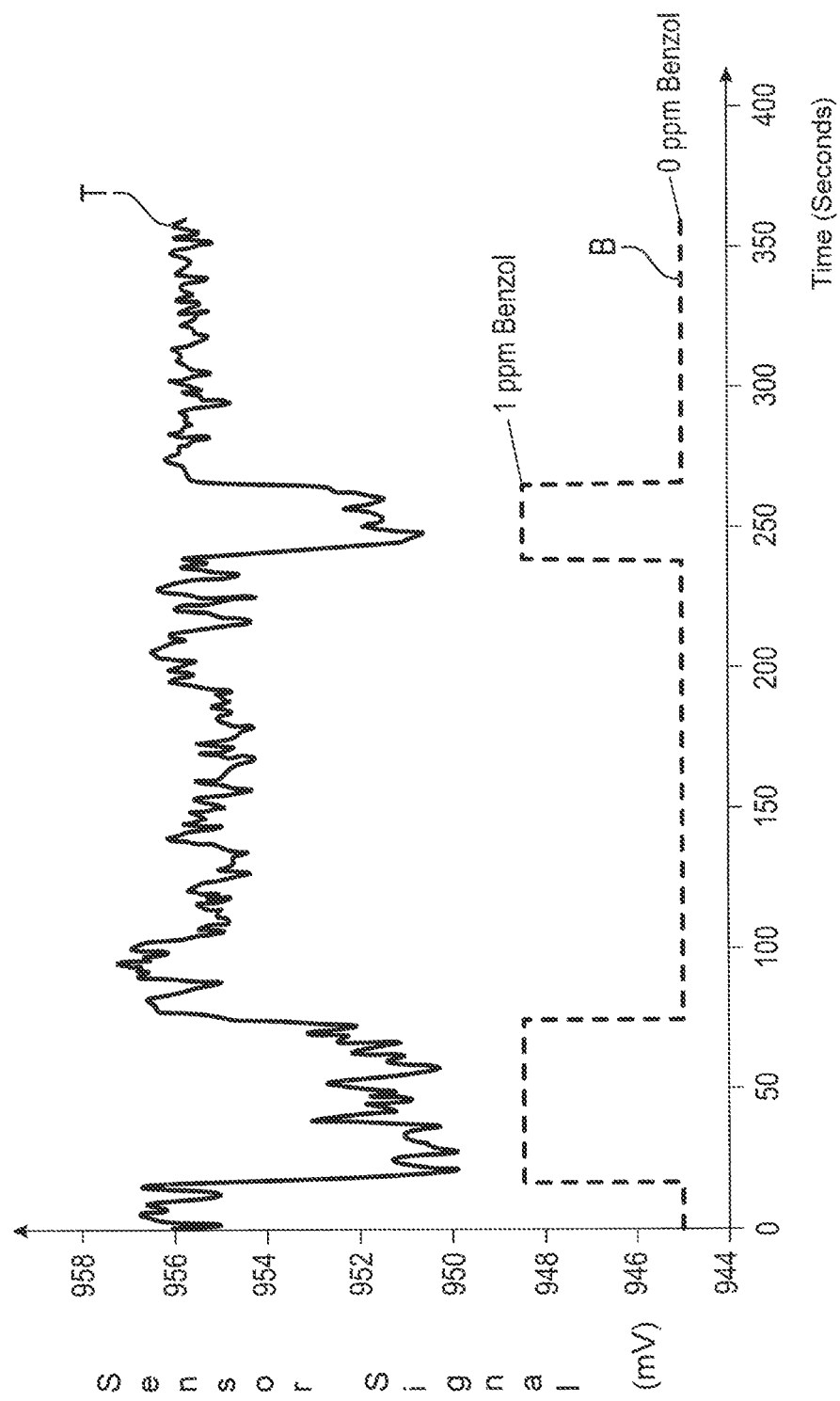
FIG. 5 is the detection of benzene by means of a gas sensor according to the present invention.

FIG. 5 shows a dynamic measured curve, which was recorded by means of a gas sensor 10, which has an analyte-binding layer 20 corresponding to one of the exemplary embodiments shown above. Such a measured curve can be obtained especially by means of an analyte-binding layer 20 as shown in FIG. 4.

The change in the work function as a function of the presence of an analyte is seen in FIG. 5. The curve T shows the work function measured by the gas sensor 10. Curve B shows the concentration of an analyte A, here benzene. The receptor is first exposed to benzene-free air. As can be seen on curve B, a benzene concentration of 1 ppm is admitted after 17 seconds. It can further be seen that the work function has changed by 5 mV immediately after the addition of benzene, namely, after about 3 sec. The flow of benzene is interrupted after 57 sec. The work function goes back to the original initial value within 4 sec. The supply of benzene is restarted after 238 sec and stopped again after 264 sec. It is seen that a reliable change occurs in the work function upon this repeated admission as well.

The present invention is not limited to one of the above-described embodiments, but may be modified in many different ways.

All the features and advantages appearing from the claims, the description and the drawings, including design details, spatial arrangements and method steps, may be essential for the present invention both in themselves and in the many different combinations.

While specific embodiments of the invention have been shown and described in detail to illustrate the application of the principles of the invention, it will be understood that the invention may be embodied otherwise without departing from such principles.

The invention claimed is:

1. A gas sensing method comprising:
   (a) providing a gas sensor comprising a measuring channel with a gas inlet and with a gas outlet, at least one receptor layer, a reference electrode and an analysis unit wherein the reference electrode is capacitively coupled with the receptor layer, the reference electrode is connected, electrically, to the analysis unit, the receptor layer is formed in the measuring channel, the measuring channel forms a dielectric layer between the receptor layer and the reference electrode, the receptor layer has a support and an analyte-binding layer, the analyte-binding layer is a self-assembling monolayer, which is comprised of a plurality of molecules, the plurality of molecules each having the general formula R1-R2-X wherein R1 is a coupling group, selected from the group consisting of sulfide, disulfide, sulfinyl, sulfino, sulfo, carbonothiol, thiosulfate, thiocyanate, isothiocyanate, and wherein the molecules of the self-assembling monolayer are coupled each via R1 to the support, the support is a layer comprised of metal, the metal is selected from the group consisting of gold, platinum, palladium, silver and copper, wherein R2 is a spacer, selected from the group consisting of alkane, alkene, alkyne, heteroalkane, heteroalkene, heteroalkyne, substitute alkanes, substituted alkenes, substituted alkynes, substituted heteroalkanes, substituted heteroalkenes, substituted heteroalkynes, ethers, amines and X is an organic or organometallic group with at least one delocalized π system, wherein X is coupled directly to the spacer R2 via a covalent bond between the spacer R2 and a member of the at least one delocalized π system; and (b) directing a gas to be tested comprising at least one volatile organic compound into the measuring channel through the gas inlet;

(c) measuring a change in capacitance between the reference electrode and the receptor layer over a first period of time; and (d) calculating a concentration of the at least one volatile organic compound of the first gas as a function of the measured change in capacitance.

2. The method of claim 1, wherein step (c) further comprises allowing intermolecular interactions between the at least one volatile organic compound and the at least one delocalized π system to move at least one π electron in the at least one delocalized π system, resulting in a shift in a dipole moment of the delocalized π system.

3. The method of claim 2, wherein step (c) further comprises transmitting the shift in dipole moment of the delocalized π system to the support via the spacer and the coupling group, resulting in a change in work function on the support.

4. The method of claim 3, wherein step (c) further comprises measuring the change in work function on the support using the analysis unit.

5. The method of claim 1, wherein step (c) further comprises measuring the change in capacitance between the reference electrode and the receptor layer over the first period of time, the measured change in capacitance being a result of intermolecular interactions between the at least one volatile organic compound and the analyte binding layer.

6. The method of claim 1, further comprising:
(e) directing a calibration gas comprising a known concentration of at least one volatile organic compound into the measuring channel through the gas inlet;
(f) measuring a change in capacitance between the reference electrode and the receptor layer over a second period of time; and
(g) adjusting the function used in step (d) to calculate the concentration of the at least one volatile organic compound of the first gas based on the change in capacitance measured in step (f) and the known concentration of the at least one volatile organic compound in the calibration gas.

7. The method of claim 1, wherein step (b) further comprises directing the gas to be tested comprising the at least one volatile organic compound into the measuring channel through the gas inlet, the at least one volatile organic compound comprising benzene.

8. The method of claim 1, wherein step (b) further comprises directing the gas to be tested comprising the at least one volatile organic compound through the measuring channel between the receptor layer and the reference electrode, causing the gas to be measured to act as a dielectric layer in a capacitor formed between the receptor layer and reference electrode.

9. The method of claim 1, wherein step (b) further comprises heating the measuring channel.

10. The method of claim 1, wherein step (c) further comprises measuring the change in capacitance between the reference electrode and the receptor layer over the first period of time using the analysis unit, the analysis unit comprising a voltage-controlled oscillator.

11. The method of claim 1, further comprising:
(h) performing wherein steps (b) through (d) while the gas sensor is being worn on a person as a personal air monitor (PAM).

* * * * *